(12) United States Patent
Krueger et al.

(10) Patent No.: US 8,232,798 B2
(45) Date of Patent: Jul. 31, 2012

(54) MAGNETIC TRACKING SYSTEM FOR AN IMAGING SYSTEM

(75) Inventors: Sascha Krueger, Hamburg (DE); Hans-Aloys Wischmann, Henstedt-Ulzburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 997 days.

(21) Appl. No.: 12/065,648

(22) PCT Filed: Aug. 28, 2006

(86) PCT No.: PCT/IB2006/052980
§ 371 (c)(1),
(2), (4) Date: Mar. 4, 2008

(87) PCT Pub. No.: WO2007/029139
PCT Pub. Date: Mar. 15, 2007

(65) Prior Publication Data
US 2008/0204012 A1    Aug. 28, 2008

(30) Foreign Application Priority Data
Sep. 8, 2005 (EP) .................................. 05108224

(51) Int. Cl.
*G01R 33/00* (2006.01)
*G01R 33/12* (2006.01)
*A61B 5/05* (2006.01)

(52) U.S. Cl. ...................... 324/261; 324/228; 600/409

(58) Field of Classification Search ............ 324/207.15–207.19, 219, 239, 244, 244.1, 258, 261, 228; 600/407, 409
See application file for complete search history.

(56) References Cited

U.S. PATENT DOCUMENTS

| | | | |
|---|---|---|---|
| 6,050,724 A | 4/2000 | Schmitz et al. | |
| 6,233,476 B1 | 5/2001 | Strommer | |
| 6,477,398 B1 * | 11/2002 | Mills | 600/409 |
| 6,534,982 B1 | 3/2003 | Jakab | |
| 6,774,624 B2 | 8/2004 | Anderson et al. | |
| 6,812,700 B2 * | 11/2004 | Fahrig et al. | 324/318 |
| 2003/0130576 A1 | 7/2003 | Seeley et al. | |
| 2003/0184285 A1 | 10/2003 | Anderson et al. | |
| 2004/0097804 A1 | 5/2004 | Sobe | |
| 2006/0055712 A1 * | 3/2006 | Anderson | 345/647 |

FOREIGN PATENT DOCUMENTS

| | | |
|---|---|---|
| EP | 0531081 A1 | 3/1993 |
| WO | WO9509562 A1 | 4/1995 |
| WO | WO9736192 A1 | 10/1997 |
| WO | WO0010456 A1 | 3/2000 |

OTHER PUBLICATIONS

MediGuide (Medical Guidance Systems), Intra-Body Navigation Solutions; Siemens and Mediguide Conclude Cooperative Agreement, From Siemens Website, Erlangen, Nov. 18, 2004.

* cited by examiner

*Primary Examiner* — Bot Ledynh

(57) ABSTRACT

A magnetic tracking system is particularly adapted for a combination with an imaging system, for example with a rotational X ray device. The magnetic tracking system includes pairs of first and second field generators that are disposed on opposite sides of a measuring volume. The first field generators may particularly be attached to a radiation source and the second field generators to a detector of the X ray device. Moreover, the first and second field generators may be constituted by coils with opposite magnetic polarity. Due to the attachment of the field generators to the X ray device, motions of the X ray device do not disturb the magnetic field in a frame of reference fixed to the imaging system.

13 Claims, 4 Drawing Sheets

MAGNETIC TRACKING SYSTEM FOR AN IMAGING SYSTEM

The invention relates to a magnetic tracking system comprising means for generating a magnetic field and for measuring it, to an investigation apparatus comprising such a magnetic tracking system, and to a method for determining positional coordinates in the field of view of an imaging system.

Magnetic tracking systems may inter alia be used in medical applications to determine the position of an object that is not directly visible, for example of a catheter in the body of a patient. An exemplary magnetic tracking system described in the WO 97/36192 (which is incorporated into the present application by reference) comprises a coil that may be attached to a medical instrument and generates a magnetic dipole field. A set of so-called "gradient coils" determines a number of independent partial derivatives of the magnetic field at a location of interest, wherein said data can be used to calculate positional coordinates of said location. Each gradient coil consists of two single coils positioned one behind the other in axial direction. To achieve a compact device, six such gradient coils are arranged at the edges of a tetrahedron. Moreover, the measuring principle can be inverted in such a way that the gradient coils generate (quadrupole) magnetic fields which are sensed by the single probe coil at the medical instrument. While magnetic tracking systems have many advantageous properties, problems arise if they are used in combination with imaging systems like rotational X-ray devices due to time-varying disturbances of the magnetic field by moving metal components of the imaging system. Moreover the required co-registration of tracking and imaging space is usually only valid for one fixed position of the imaging system. These complications have a high share in the still remaining low acceptance of magnetic tracking systems in clinical practice.

Based on this situation it was an object of the present invention to provide means for the determination of positional coordinates, said means being particularly suited for a combination with (rotational) medical imaging systems.

According to its first aspect, the invention relates to a magnetic tracking system that can be used to determine positional coordinates at a point of interest, wherein "positional coordinates" shall by definition comprise any quantitative information about the position and/or orientation of an object of interest at a certain point in space. Positional coordinates may for example comprise the Cartesian coordinates x, y, z of the position and the polar coordinates φ, ψ of the orientation of a catheter tip. The magnetic tracking system according to the present invention comprises the following components:
  a) At least one first field generator and at least one second field generator for commonly generating a spatially varying magnetic field in a measuring volume between said field generators. The field generators may particularly be constituted by electrical coils which have the advantage that the direction, magnitude and temporal course of the magnetic field can readily be controlled by the electrical currents applied to the coils.
  b) At least one detector probe for measuring said magnetic field in the measuring volume.

An advantage of the aforementioned magnetic tracking system is that the spatially varying magnetic field is generated in the region between two cooperating field generators. The spatial course of the magnetic field in this region is therefore more unique and exhibits a stronger gradient making it less prone to disturbances and more reproducible than the magnetic fields generated by usual field generators which are designed as substantially punctual field sources. The requirement to position two field generators at opposite sides of a measuring volume turns out to be no severe restriction in most medical applications because other components (e.g. elements of an imaging system) have to be disposed around the measuring volume anyway. It should be noted that two field generators are considered to be disposed "on opposite sides of a measuring volume" in this context if the lines connecting the centers of said field generators with the center of the measuring volume enclose an angle of about 90° to about 270° (with an angle of 180° corresponding to an exactly opposite arrangement).

The distance between the first and the second field generator is preferably more than five times, more preferably more than 30 times, and most preferably more than 200 times the axial length of said generators. By definition, the "axial length of the field generators" is measured in the direction of the line connecting the first and the second field generator in their final arrangements. If the field generators do not have identical dimensions, the "axial length of the field generators" shall be defined as the maximum of their individual lengths. In typical applications, the distance between the first and the second field generator will range from about 0.5 m to 3 m.

There are several different ways to arrange or orient the magnetic field generators. In a preferred embodiment of the invention, they are arranged in such a way that the generated magnetic field has a spatially unique gradient in the measuring volume. By determining said gradient it is then possible to unambiguously derive the desired positional coordinates of a point of interest in the measuring volume.

In a particular embodiment of the invention, the first and the second field generators are oppositely oriented magnetic dipoles, for example a so-called "Maxwell coil pair". Such an arrangement has the advantage to generate a strong and uniform gradient of the magnetic field in a region between the two field generators similar to the z-gradient in magnetic resonance imaging systems.

In another embodiment, at least one of the first and the second field generators comprises a pair of magnetic dipoles that are arranged in axial alignment one behind the other with opposite or with the same polarity. Preferably both the first and second field generator are designed in such a way and arranged spaced apart from each other and parallel to each other, for example in an arrangement that is known as "saddle coil pair". By a suitable combination of the field generators it is then possible to generate a unique overall magnetic field.

Of course first and second field generators of the kinds described above may be combined, for example in a combined arrangement of Maxwell coil pairs and saddle coil pairs.

According to a second aspect, the invention relates to an investigation apparatus with an imaging system for the generation of images of an object, e.g. a patient, in a field of view. Said investigation apparatus further comprises a magnetic tracking system with
  a) At least one first field generator and at least one second field generator for commonly generating a spatially varying magnetic field in a measuring volume between said field generators, wherein the measuring volume at least partially overlaps with the field of view of the imaging system.
  b) At least one detector probe for measuring said magnetic field in the measuring volume.

The magnetic tracking system may preferably be realized by one of the embodiments of a magnetic tracking system described above. As the field generators of the magnetic tracking system are arranged on different sides of the measuring volume/field of view, the generated magnetic field is less prone to disturbances by (ferro-)magnetic or conductive components (generating eddy currents) of the imaging system.

In general, the imaging system of the investigation apparatus may be any device that is adapted to generate images of an object, for example a photographic device, an ultrasound device, a magnetic resonance imaging (MRI) device, a scintillator device, a PET scanner etc. The imaging system may in particular be an X-ray device with a radiation source and an X-ray detector that are disposed on opposite sides of the field of view. X-ray devices are widely used during medical interventions which require a parallel application of magnetic tracking systems for determining the position of an instrument like a catheter.

The imaging system may especially be a rotational X-ray device, wherein the radiation source and the X-ray detector are attached to a common movable member, for example a rotatable C-arm. A movable or rotatable arrangement of X-ray source and detector is commonly used to generate X-ray projections from different directions, thus allowing to select on optimal point of view and/or to generate three-dimensional images.

According to a preferred embodiment of the investigation apparatus, the field generators are attached to movable members of the imaging system. In particular, the first field generator may be attached to the radiation source and the second field generator may be attached to the X-ray detector of a rotational X-ray device (note that the roles of the first and second field generator are symmetrical, i.e. that they may be exchanged). If usual magnetic tracking systems are used in combination with rotational X-ray devices, the time-varying and unpredictable disturbances introduced by the movable metal components of said devices pose severe problems. If the field generators are however attached to the main movable components, the magnetic field generated by the field generators moves in synchronicity with the disturbances, thus remaining stationary in a frame of reference fixed to the moving components. Tracking and imaging space remain correctly co-registered for any position of the imaging system.

The invention further relates to a method for the determination of positional coordinates in the field of view of an imaging system that has movable imaging components, for example for the determination of the position and/or orientation of a catheter tip in the field of view of a rotational X-ray device. The method may particularly be executed with an investigation apparatus of the kind described above. The method comprises the following steps:

a) Attaching at least one first field generator to a first movable imaging component of the imaging system and at least one second field generator to a second movable imaging component of the imaging system, wherein the first and the second movable imaging components are arranged on opposite sides of the field of view.

b) Generating a spatially varying magnetic field within the field of view with the help of said first and second field generators.

c) Measuring the aforementioned magnetic field at a position of interest and calculating the positional coordinates corresponding to said position from said measurement.

The method comprises in general form the steps that can be executed with an investigation apparatus of the kind described above. Therefore, reference is made to the preceding description for more information on the details, advantages and improvements of that method.

These and other aspects of the invention will be apparent from and elucidated with reference to the embodiment(s) described hereinafter. These embodiments will be described by way of example with the help of the accompanying drawings in which.

Figure 8:
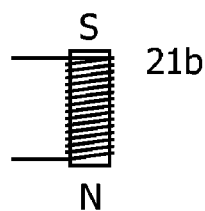
Figure 8:
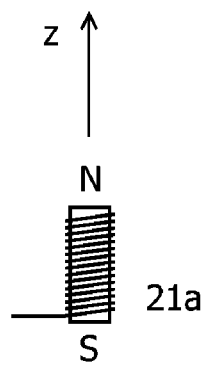
Figure 9:
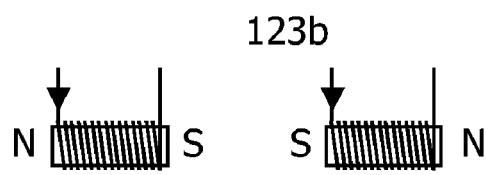
Figure 9:
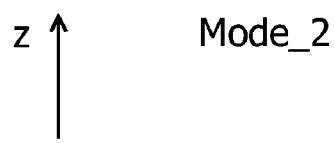
Figure 9:
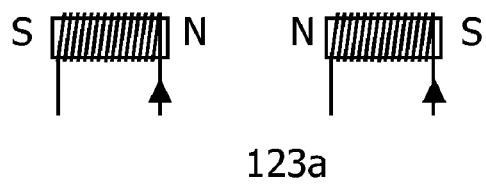

FIG. 8 schematically shows the arrangement of a Maxwell coil pair;

FIG. 9 schematically shows the arrangement of a saddle coil pair driven in Mode_1.

Like reference numbers in the Figures refer to identical or similar components.

Figure 1:
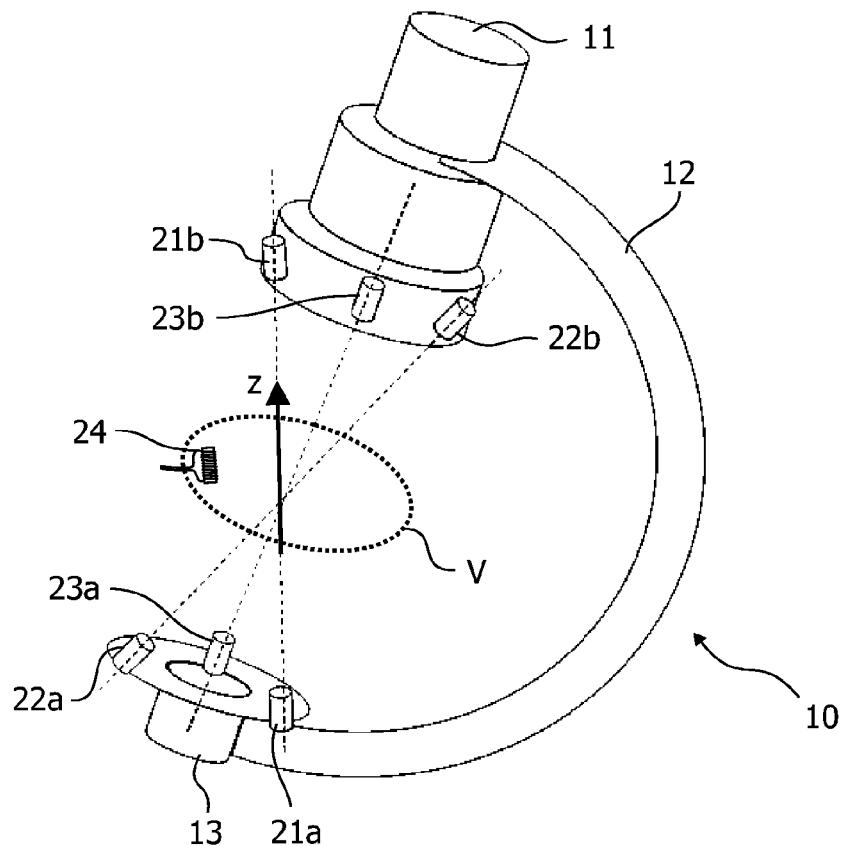
FIG. 1 shows a schematic perspective view of a C-arm X-ray device equipped with a magnetic tracking system according to a first embodiment of the present invention.

FIG. 1 shows in a perspective view a rotational X-ray device 10 which comprises as usual a radiation source 13 and an X-ray detector 11 that are facing each other from opposite sides of a field of view and are fixed to opposite ends of a C-arm 12. The C-arm 12 can be rotated about an axis (not shown) for varying the projection direction accordingly.

In order to determine the position and/or orientation of an object in the field of view, the rotational X-ray device 10 is equipped with a magnetic tracking system according to the present invention. Said magnetic tracking system comprises, in the shown embodiment, three pairs of field generators in the form of coils, wherein each pair consists of a first field generator or coil 21a, 22a and 23a, respectively, which is attached to the X-ray source 13, and a second field generator or coil 21b, 22b and 23b, respectively, which is attached to the X-ray detector 11 (preferably e.g. close to its image intensifier or the flat panel detector unit in modern digital x-ray imaging systems). Each pair of field generators of said arrangement, for example the first field generator 21a and the second field generator 21b, constitutes a so-called "Maxwell coil pair" if the current is directed through the coils in such a way that they have an opposite magnetic polarity.

Figure 2:
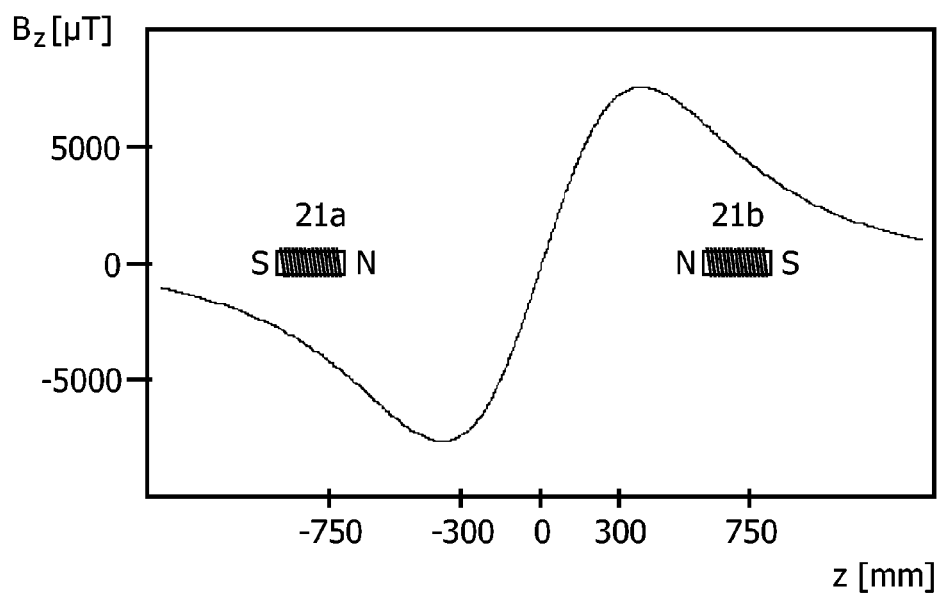
FIG. 2 depicts the course of the z-component of the magnetic field along the z-direction of FIG. 1.

FIG. 8 shows separately the arrangement of the Maxwell coil pair 21a, 21b (the drawing is not to scale). Moreover, FIG. 2 shows the course of the z-component $B_z$ of the corresponding magnetic field B along the z-axis. Said z-axis points along the axis of coils 21a, 21b from the X-ray source 13 to the X-ray detector 11 (FIG. 1) with the X-ray source 13 being arranged at z=−750 mm and the X-ray detector 11 being arranged at z=750 mm. As can be seen from FIG. 2, the magnetic field has a unique, uniform, and strong gradient in an intermediate region of about ±300 mm. This region can then be used as a measuring volume V (FIG. 1) to determine the positional coordinates of an object of interest.

For the aforementioned measurements, a detector probe or coil 24 can be used which is brought into the measuring volume V. Such a coil is typically very small and attached to a medical instrument like a catheter. By measuring the magnetic field (or at least one component of it) at the position of the coil 24, it is possible to calculate the positional coordinates of said coil according to principles known to a person skilled in the art. The coordinates are preferably expressed in a Cartesian coordinate system which is fixed to the imaging system 10, because the magnetic field does change in said system during rotational movements.

Instead of the Maxwell coil pair described above, other arrangements of first and second field generators may be used, too. FIG. 9 shows for example a possible arrangement which is known as "saddle coil pair" and used for instance in the area of magnetic resonance tomography. The first field generator 123a of this arrangement consists of two coils arranged in axial alignment one behind the other with opposite magnetic polarity. The second field generator 123b is identical to the first one but shifted in direction of the shown z-axis (which is perpendicular to the axes of the coils) and opposite in polarities.

The polarities shown in FIG. 9 are achieved if the four coils are driven with current in a "Mode_2" as indicated by the arrows. As each coil can be individually supplied with current, many other modes are possible, too. A "Mode_1" may for example be achieved if the current direction (and thus polarity) of one coil is inverted in each field generator 123a, 123b of FIG. 9 (cf. FIG. 7). In general, each mode generating a linear independent configuration of the magnetic field is advantageous as it allows an independent measurement of positional coordinates.

FIG. 3 once again represents schematically the first embodiment of a magnetic tracking system with three Maxwell coil pairs 21, 22, 23 arranged at different angles with respect to each other. In contrast to this, FIG. 4 represents schematically a second embodiment of a magnetic tracking system with one Maxwell coil pair 121a, 121b and two saddle coil pairs 122a, 122b and 123a, 123b, respectively (only one loop is indicated of the corresponding coils).

Figure 3:
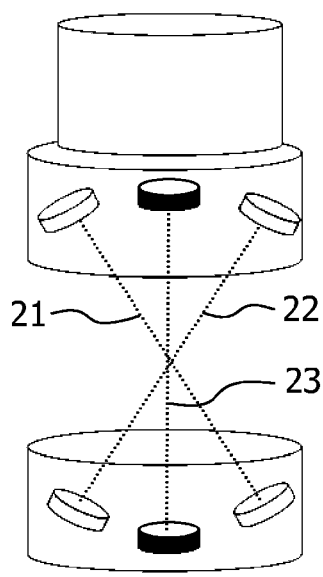
FIG. 3 shows schematically the three Maxwell coil pairs used in the first embodiment of FIG. 1.
Figure 4:
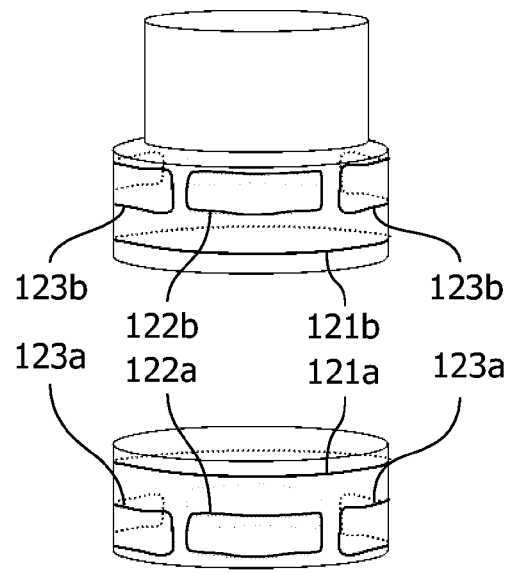
FIG. 4 shows schematically one Maxwell coil pair and two saddle coils pairs used in a second embodiment of the invention.
Figure 5:
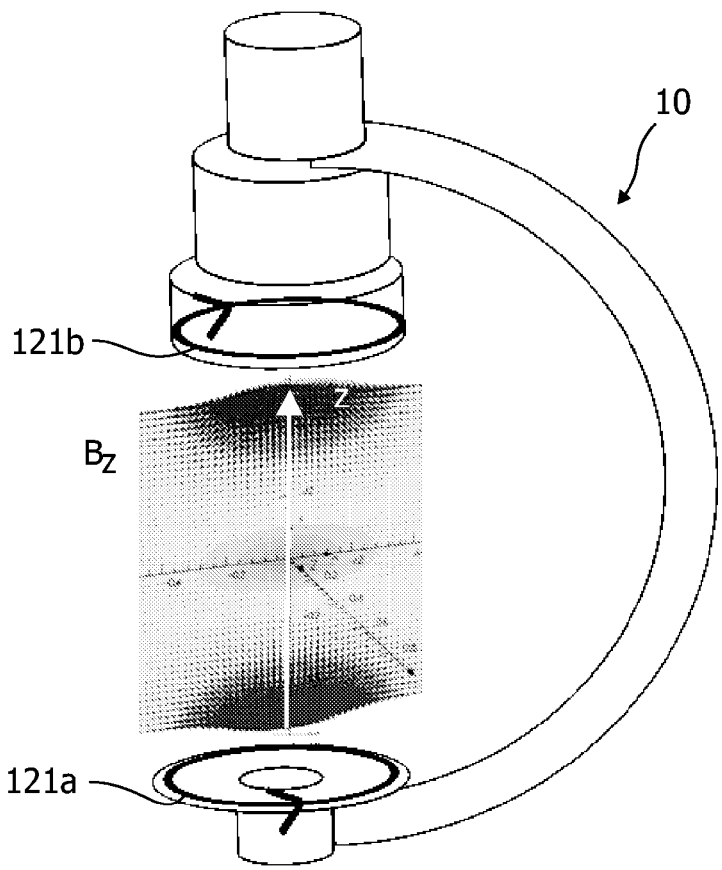
FIG. 5 illustrates the z-component of the magnetic field generated by the Maxwell coil pair of FIG. 4.

FIG. 5 illustrates the z-component $B_z$ of the magnetic field which is generated by the Maxwell coil pair 121a, 121b of FIG. 4 (note that similar fields will be generated by Maxwell coils 21, 22, 23 of FIG. 3).

Figure 6:
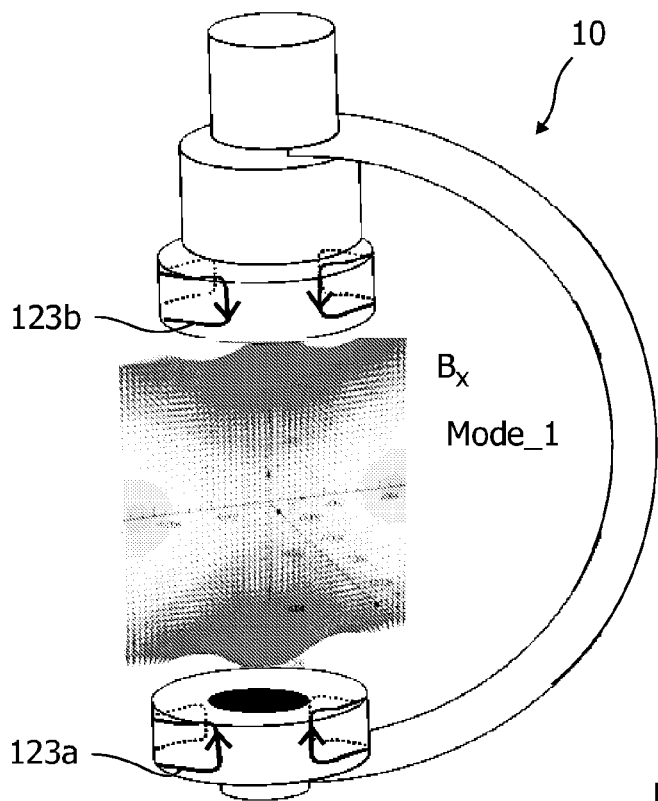
FIG. 6 illustrates the x-component of the magnetic field generated by a saddle coil pair of FIG. 4 in a first mode.
Figure 7:
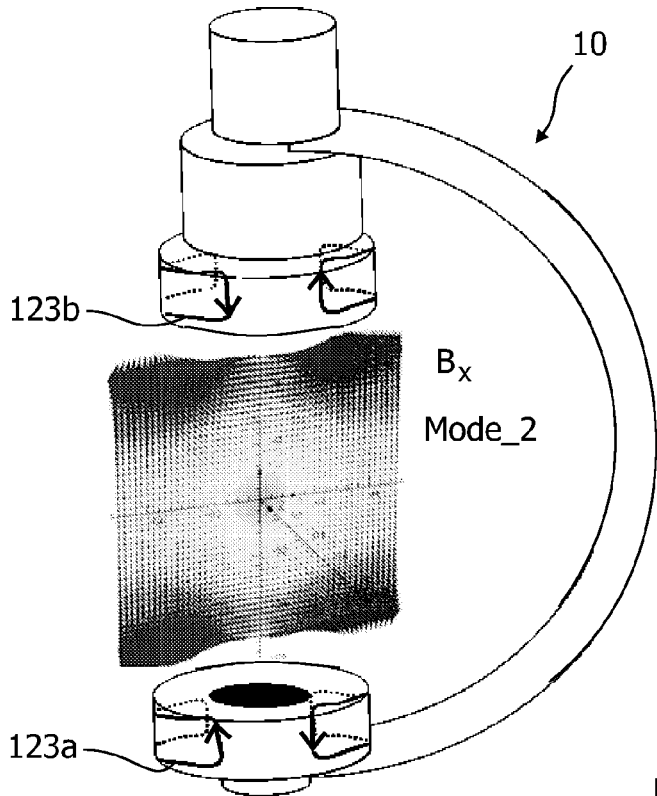
FIG. 7 illustrates the x-component of the magnetic field generated by a saddle coil pair of FIG. 4 in a second mode.

In a similar way, FIGS. 6 and 7 illustrate the x-component $B_x$ of the magnetic field generated by the saddle coil pair 123a, 123b of FIG. 4 in a first "Mode_1" (FIG. 6) and a second "Mode_2" (FIG. 7). Besides a rotation of 90° about the z-axis, similar pictures can be generated for the other saddle coil pair 122a, 122b.

Other modifications of the described embodiments may comprise different numbers and/or arrangements of the first and second field generators with respect to the imaging system. Moreover, the roles of the generators and detectors of the magnetic field may be exchanged. It should also be noted that the application of the present invention is not restricted to the described examples or to medical applications.

Finally it is pointed out that in the present application the term "comprising" does not exclude other elements or steps, that "a" or "an" does not exclude a plurality, and that a single processor or other unit may fulfill the functions of several means. The invention resides in each and every novel characteristic feature and each and every combination of characteristic features. Moreover, reference signs in the claims shall not be construed as limiting their scope.

The invention claimed is:

1. A magnetic tracking system comprising:
   a) at least one first field generator and at least one second field generator for commonly generating a spatially varying magnetic field in a measuring volume between said field generators for tracking an object in a field of view; and
   b) at least one detector probe for measuring said magnetic field in the measuring volume,
   wherein the at least one first field generator and the at least one second field generator are attached to movable members of an imaging system on opposite sides of the field of view.

2. The magnetic tracking system according to claim 1, wherein a distance between the at least one first field generator and the at least one second field generator corresponds to more than five times an axial length of the at least one first field generator and the at least one second field generator.

3. The magnetic tracking system according to claim 1, wherein the magnetic field has a spatially unique gradient in the measuring volume.

4. A magnetic tracking system comprising:
   a) at least one first field generator and at least one second field generator for commonly generating a spatially varying magnetic field in a measuring volume between said field generators for tracking an object in a field of view; and
   b) at least one detector probe for measuring said magnetic field in the measuring volume,
   wherein the at least one first field generator and the at least one second field generator are attached to movable members of an imaging system on opposite sides of the field of view, and
   wherein the at least one first field generator and the at least one second field generator are oppositely oriented magnetic dipoles.

5. The magnetic tracking system according to claim 1, wherein the at least one first field generator and the at least one second field generator comprises a pair of magnetic dipoles disposed in axial alignment with a same or with an opposite polarity.

6. The magnetic tracking system according to claim 1, wherein the at least one first field generator and the at least one second field generator are constituted by electrical coils.

7. An investigation apparatus comprising an imaging system for the generation of images of an object in a field of view and a magnetic tracking system with
   a) at least one first field generator and at least one second field generator for commonly generating a spatially varying magnetic field in a measuring volume between the at least one first field generator and the at least one second field generator, wherein the measuring volume at least partially overlaps with the field of view; and
   b) at least one detector probe for measuring said magnetic field in the measuring volume,
   wherein the at least one first field generator and the at least one second field generator are attached to movable members of the imaging system on opposite sides of the field of view.

8. An investigation apparatus comprising an imaging system for the generation of images of an object in a field of view and a magnetic tracking system with
   a) at least one first field generator and at least one second field generator for commonly generating a spatially varying magnetic field in a measuring volume between the at least one first field generator and the at least one second field generator, wherein the measuring volume at least partially overlaps with the field of view; and
   b) at least one detector probe for measuring said magnetic field in the measuring volume,
   wherein the at least one first field generator and the at least one second field generator are attached to movable members of the imaging system on opposite sides of the field of view, and wherein the imaging system comprises an X ray device with a radiation source and an X ray detector which are disposed at opposite sides of the field of view and attached to a common movable member.

9. The investigation apparatus according to claim 7, wherein the at least one first field generator and the at least one second field generator are attached to movable members of the imaging system, wherein the movable members include a radiation source and an X ray detector of an X ray device.

10. A method for the determination of positional coordinates in a field of view of an imaging system with movable imaging components, comprising:
  a) attaching at least one first field generator and at least one second field generator to the movable imaging components on opposite sides of the field of view;
  b) generating a spatially varying magnetic field within the field of view; and
  c) measuring said magnetic field at a position of interest and inferring positional coordinates corresponding to said position of interest from said measurement.

11. The method according to claim 10, wherein the method is executed with an investigation apparatus comprising an imaging system for generation of images of an object in the field of view and a magnetic tracking system with
  a) at least one first field generator and at least one second field generator for commonly generating the spatially varying magnetic field in a measuring volume between said at least one first field generator and said at least one second field generator, wherein the measuring volume at least partially overlaps with the field of view; and
  b) at least one detector probe for measuring said magnetic field in the measuring volume.

12. The magnetic tracking system according to claim 1, wherein a distance between the at least one first field generator and the at least one second field generator corresponds to more than 30 times an axial length of the at least one first field generator and the at least one second field generator.

13. The magnetic tracking system according to claim 1, wherein a distance between the at least one first field generator and the at least one second field generator corresponds to more than 200 times an axial length of the at least one first field generator and the at least one second field generator.

* * * * *